US012539168B2

(12) United States Patent
Kerr et al.

(10) Patent No.: US 12,539,168 B2
(45) **Date of Patent: *Feb. 3, 2026**

(54) MEDICAL DEVICE HAVING EXTENDABLE MEMBERS

(71) Applicant: BOSTON SCIENTIFIC SCIMED, INC., Maple Grove, MN (US)

(72) Inventors: Shawn Kerr, Lancaster, MA (US); John A. Hingston, Framingham, MA (US); Tara A. Jarobski, North Oxford, MA (US); Gene T. Storbeck, Franklin, MA (US); Allison M. Pearlman, Holden, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1085 days.

This patent is subject to a terminal disclaimer.

(21) Appl. No.: 17/032,939

(22) Filed: Sep. 25, 2020

(65) Prior Publication Data

US 2021/0015553 A1 Jan. 21, 2021

Related U.S. Application Data

(63) Continuation of application No. 15/198,666, filed on Jun. 30, 2016, now Pat. No. 10,799,287.

(60) Provisional application No. 62/189,582, filed on Jul. 7, 2015.

(51) Int. Cl.

*A61B 18/14* (2006.01)
*A61B 18/00* (2006.01)

(52) U.S. Cl.

CPC .. *A61B 18/1492* (2013.01); *A61B 2018/0016* (2013.01); *A61B 2018/00214* (2013.01); *A61B 2018/00267* (2013.01)

(58) Field of Classification Search

CPC ........ A61B 18/1492; A61B 2018/0016; A61B 2018/00214; A61B 2018/00267

See application file for complete search history.

(56) References Cited

U.S. PATENT DOCUMENTS

| | | | | |
|---|---|---|---|---|
| 4,709,698 A | | 12/1987 | Johnston et al. | |
| 5,238,004 A | | 8/1993 | Sahatjian et al. | |
| 5,702,438 A | * | 12/1997 | Avitall | A61N 1/056 607/128 |
| 5,860,974 A | | 1/1999 | Abele | |
| 6,508,803 B1 | | 1/2003 | Horikawa et al. | |
| 7,153,315 B2 | | 12/2006 | Miller | |

(Continued)

*Primary Examiner* — Linda C Dvorak
*Assistant Examiner* — Christine A Dedoulis
(74) *Attorney, Agent, or Firm* — Seager, Tufte & Wickhem, LLP

(57) ABSTRACT

This disclosure provides design, material, manufacturing method, and use alternatives for medical devices. An example medical device includes a scaffold including a central member and a plurality of extension members extending away from the central member. The central member includes a plurality of discrete attachment locations corresponding to each of the plurality of extension members and each of the plurality of extension members is pivotably coupled to the central member at a corresponding discrete attachment location. The medical device also includes a covering substantially surrounding the scaffold and an electrode located at a distal end of each of the plurality of extension members. Each electrode extends through at least a portion of the covering.

20 Claims, 10 Drawing Sheets

(56) References Cited

U.S. PATENT DOCUMENTS

| | | | | |
|---|---|---|---|---|
| 7,291,146 | B2 | 11/2007 | Steinke et al. | |
| 7,371,235 | B2 * | 5/2008 | Thompson | A61B 18/1492 606/41 |
| 7,632,268 | B2 | 12/2009 | Edwards et al. | |
| 8,167,845 | B2 | 5/2012 | Wang et al. | |
| 8,951,251 | B2 | 2/2015 | Willard | |
| 9,186,212 | B2 * | 11/2015 | Nabutovsky | A61B 5/0538 |
| 9,345,422 | B2 | 5/2016 | Rothenberg | |
| 9,402,684 | B2 | 8/2016 | Mathur et al. | |
| 9,408,661 | B2 | 8/2016 | Haverkost | |
| 9,408,663 | B2 | 8/2016 | Hall et al. | |
| 9,433,760 | B2 | 9/2016 | Subramaniam et al. | |
| 9,463,062 | B2 | 10/2016 | Smith et al. | |
| 2010/0168743 | A1 | 7/2010 | Stone et al. | |
| 2013/0116685 | A1 | 5/2013 | Deem et al. | |
| 2014/0031810 | A1 | 1/2014 | Mahvi et al. | |
| 2015/0018820 | A1 | 1/2015 | Cao et al. | |
| 2015/0351836 | A1 * | 12/2015 | Prutchi | A61B 18/1492 606/41 |
| 2016/0113582 | A1 * | 4/2016 | Altmann | A61M 25/09 606/41 |

* cited by examiner

MEDICAL DEVICE HAVING EXTENDABLE MEMBERS

CROSS-REFERENCE TO RELATED APPLICATIONS

This application is a continuation of U.S. application Ser. No. 15/198,666, filed Jun. 30, 2016, which claims priority under 35 U.S.C. § 119 to U.S. Provisional Application Ser. No. 62/189,582, filed Jul. 7, 2015, the entirety of which is incorporated herein by reference.

TECHNICAL FIELD

The present disclosure pertains to medical devices, and methods for manufacturing medical devices. More particularly, the present disclosure pertains to elongated intracorporeal medical devices connected with other structures, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods.

BRIEF SUMMARY

This disclosure provides design, material, manufacturing method, and use alternatives for medical devices. An example medical device comprises:

a scaffold including a central member and a plurality of extension members extending away from the central member, wherein the central member includes a plurality of discrete attachment locations corresponding to each of the plurality of extension members and wherein each of the plurality of extension members is pivotably coupled to the central member at a corresponding discrete attachment location;

a covering substantially surrounding the scaffold; and an electrode located at a distal end of each of the plurality of extension members, wherein each electrode extends through at least a portion of the covering.

Alternatively or additionally to any of the embodiments above, wherein the central member has a longitudinal axis, and wherein the plurality of discrete attachment locations are spaced along the longitudinal axis.

Alternatively or additionally to any of the embodiments above, wherein the scaffold is collapsible.

Alternatively or additionally to any of the embodiments above, wherein when the scaffold is collapsed the distal ends of the extension members are positioned substantially alongside the central member.

Alternatively or additionally to any of the embodiments above, wherein the scaffold has a first position wherein the extension members are pivoted in a substantially distal facing direction and wherein the scaffold has a second position wherein the extension members extend radially from the central member, and wherein the scaffold can shift between the first position and the second position.

Alternatively or additionally to any of the embodiments above, wherein the extension members are metallic.

Alternatively or additionally to any of the embodiments above, wherein the central member, the extension members, or both include a wire.

Alternatively or additionally to any of the embodiments above, wherein the covering is a polymer.

Alternatively or additionally to any of the embodiments above, wherein the plurality of extension members includes a first extension member having a first length and a second extension member having a second length and wherein the first length is different than the second length.

Alternatively or additionally to any of the embodiments above, wherein the central member includes a proximal portion, a distal portion and a middle portion located between the proximal and distal portions, wherein each of the proximal, middle and distal portions include at least one extension member attached thereto, and wherein the lengths of the at least one extension member attached to the proximal and distal portions are shorter than the at least one extension member attached to the middle portion.

Alternatively or additionally to any of the embodiments above, wherein the electrodes are substantially flush with an outer surface of the covering.

Alternatively or additionally to any of the embodiments above, wherein the electrodes include a bipolar electrode, a unipolar electrode or both.

Alternatively or additionally to any of the embodiments above, wherein the electrodes are coupled to an energy source.

Alternatively or additionally to any of the embodiments above, wherein the scaffold has a first configuration and a second configuration, and wherein an actuation member is capable of shifting the scaffold between the first and the second positions.

Alternatively or additionally to any of the embodiments above, further comprising a catheter shaft coupled to the scaffold, wherein the catheter shaft include a connection member capable of coupling to a power element.

Another example medical device comprises:

a conductive assembly having a first collapsed configuration and a second expanded configuration, wherein the conductive assembly is capable of being shifted between the first collapsed configuration and the second expanded configuration;

wherein the conductive assembly includes a central member, a plurality of extension members extending away from the central member, an electrode coupled to a distal portion of the extension members, and a covering substantially surrounding the conductive assembly; and wherein the electrode extends through at least a portion of the covering.

Alternatively or additionally to any of the embodiments above, wherein the extension members are pivotably coupled to the central member.

Alternatively or additionally to any of the embodiments above, wherein the central member includes a plurality of discrete attachment locations corresponding to each of the plurality of extension members and wherein each of the plurality of extension members is coupled to the central member at a corresponding discrete attachment location Alternatively or additionally to any of the embodiments above, wherein the extension members are metallic.

Alternatively or additionally to any of the embodiments above, wherein the covering is a polymer.

Alternatively or additionally to any of the embodiments above, wherein the electrodes are substantially flush with an outer surface of the covering.

Another medical device comprises:

a scaffold including a central member and a plurality of extension members extending away from the central member, wherein the central member includes a plurality of extension members pivotably coupled to the central member;

a covering substantially surrounding the scaffold;

an electrode located at a distal end of each of the plurality of extension members, wherein each electrode extends through at least a portion of the covering;

a catheter shaft coupled to the scaffold; and wherein the catheter shaft includes a connection member capable of coupling to an RF generator.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
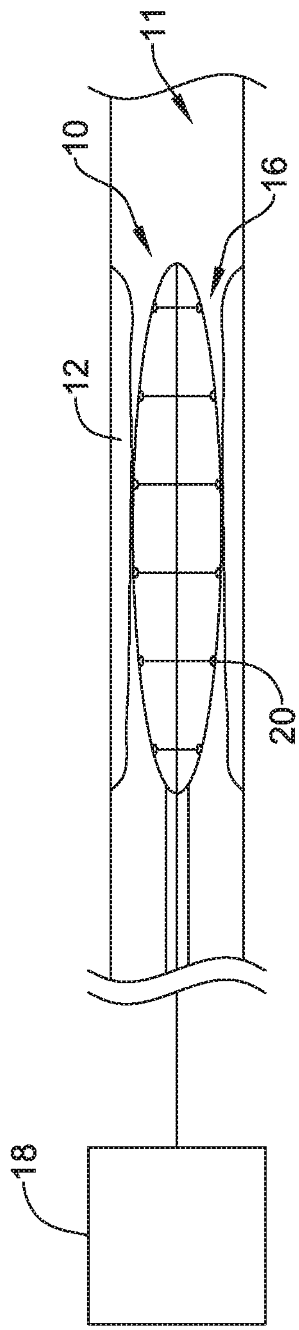
FIG. 1 is an illustration of an example medical device positioned within a body lumen.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

While the devices and methods described herein are discussed relative to ablation of strictures in the pancreatico-biliary tree, it is contemplated that the devices and methods described herein may be used in other applications where modulation and/or ablation is desired.

Cholangitis is an infection of the biliary tract that may cause severe illness and/or death. In some instances, cholangitis may be caused by one or more obstructions occurring in a body lumen. For example, pancreatic duct strictures may cause a narrowing or occlusion in the biliary tree (e.g. in the biliary duct), resulting in the development of cholangitis. Further, pancreatic duct strictures present one of the most challenging diagnostic and therapeutic pancreatic disorders. Standard treatment of strictures in the pancreatico-biliary tree often includes stenting. However, in some instances additional therapies may be utilized alone or in conjunction with stenting to treat strictures occurring in the pancreatico-biliary tree. For example, in some instances it may be desirable to apply radiofrequency (hereinafter "RF") energy to eliminate strictures, thereby restoring patency to an occluded duct. The medical devices and methods for using those medical devices disclosed herein may apply RF energy to occlusions or strictures, thereby restoring patency to occluded ducts and/or vessels occurring within the body (e.g. in the biliary tree).

FIG. 1 is a schematic view of an illustrative stricture ablation assembly 10 located within stricture 12 in an example body lumen 11. Stricture 12 may represent a stricture occurring in the bile duct of the pancreatico-biliary tree. Assembly 10 may include a conductive assembly 16 for delivering ablation energy to stricture 12, the details of which can be better seen in subsequent figures. A proximal end of conductive assembly 16 may be connected to a control and power element 18 (e.g. an RF generator), which supplies the desired electrical energy to activate one or more electrodes 20 of the conductive assembly 16. The control and power element 18 may include monitoring elements to monitor parameters such as power, temperature, voltage and/or shape and other suitable parameters as well as suitable controls for performing the desired procedure. In some instances, power element 18 may control the amount of energy delivered to electrodes 20.

Figure 2:
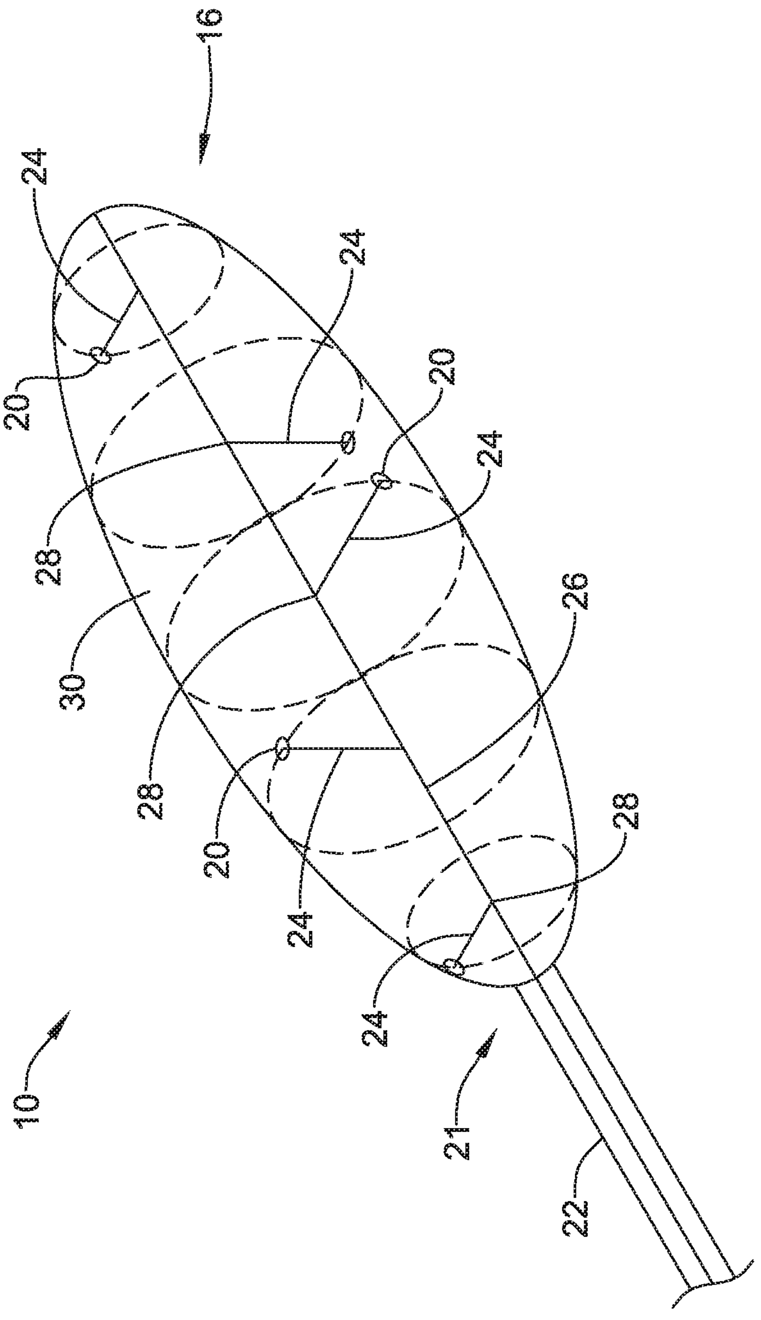
FIG. 2 is a perspective view of an example medical device.

FIG. 2 is an illustrative embodiment of a distal end of stricture ablation assembly 10. The assembly 10 may include an elongate shaft 22 having a distal end region 21 coupled to conductive assembly 16. Elongate shaft 22 may be, for example, a catheter shaft including a lumen. In some instances, elongate shaft 22 may provide the desired stiffness and/or columnar strength to support and/or advance ablation assembly 10 through the vasculature (e.g. biliary tree), for example.

FIG. 2 shows conductive assembly 16 including one or more extension members 24 disposed radially about a central member 26. Extension members 24 may be attached to central member 26 at one or more discrete attachment locations 28 positioned longitudinal axis of central member 26. Conductive assembly 16 may also include electrodes 20 coupled to the distal portion (e.g. distal end) of one or more of the extension members 24. Additionally, conductive assembly 16 may include a covering 30 substantially surrounding a portion of central member 26, extension members 24 and/or electrodes 20. Stricture ablation assembly 10 (and the elements included therein) may be considered and/or referred to herein as a "scaffold."

As shown in FIG. 2, extension members 24 may be disposed so they extend radially away from the central member 26. There may be two, three, four, five (as shown) or more extension members 24 and they may be spaced equally along the longitudinal axis of central member 26 or may be spaced unequally along the longitudinal axis of central member 26. Individual extension members 24 may be attached to central member 26 at discrete attachment locations 28. In some instances, each individual extension member 24 may attach to central member 26 at a single, corresponding discrete attachment location 28 (e.g. at an attachment location 28 in which no other extension members 24 are attached). In other instances, one or more individual extension members 24 may be attached to central member 26 at the same single discrete attachment location 28 (e.g. multiple extension members 24 attached to at a single attachment location 28).

In some instances, extension members 24 may not be symmetrically distributed around the circumference of central member 26. In other instances, extension members 24 may be symmetrically distributed around the circumference of central member 26. In yet other instances, extension members 24 may be distributed in a helical, spiral or other arrangement around central member 26.

In some embodiments disclosed herein, central member 26 and/or extension members 24 may be defined as a wire. For example, central member 26 and/or extension members 24 may be constructed from a conductive metal. Further, central member 26 and/or extension member 24 may be solid wires. However, it is contemplated that central member 26 and/or extension members 24 may include a lumen extending within and along at least a portion of the central member 26 and/or extension members 24. It is further contemplated that central member 26 and/or extension members 24 may be include a variety of shapes, geometries, cuts, slits, apertures, openings and/or combinations thereof.

As shown in FIG. 2, one or more electrodes 20 may be attached to the distal portion (e.g. distal end) of one or more of the extension members 24. In some instances, electrodes 20 may be separate pieces coupled (e.g. attached) to extension members 24. In other instances, electrodes 20 may be formed coincident with the extension members 24 (e.g. constructed from single pieces of material to form monolithic extension member/electrode 24/20 assemblies). Although FIG. 2 shows single electrodes 20 attached to the distal ends of the extension members 24, it is contemplated that more than one electrode may be attached to one or more of extension members 24.

Electrodes 20 may include a variety of shapes and/or configurations. For example, electrodes 20 may be substantially disk-shaped (as shown in FIG. 2). However, it is contemplated that electrodes 20 may be spherical, ovular, rectangular, square, or the like. Furthermore, electrodes 20 may be a variety of thicknesses and include a variety of flexibility profiles.

As stated above, central member 26, extension member 24 and/or electrode 20 may be electrically conductive. For example, in some instances, the central member 26 and extension member 24 may form a portion of the conductive path to one or more of electrodes 20. For example, central member 26 and extension member 24 may provide a conductive path for RF energy to be delivered to an electrode 20. However, it is contemplated that some embodiments disclosed herein may include a separate conductive path extending between central member 26, extension members 24 and/or electrodes 20. Such a separate conductive path may be a separate wire, a conductive strip or the like formed on one or more of central member 26, extension members 24 and/or electrodes 20.

Conductive paths discussed herein may connect one or more electrodes 20 with power element 18. Further, in some instances central member 26 may extend in a proximal direction and be coupled to power element 18. For example, central member 26 may extend within a lumen of elongate shaft 22. However, it is further contemplated that central member 26 may extend along the outer surface of elongate shaft 22 or be embedded within elongate shaft 22.

As stated above, central member 26, extension members 24 and/or electrodes 20 may be substantially surrounded by covering 30. Covering 30 may include a polymeric material that is designed to flex and/or conform to the shape of central member 26, extension members 24 and/or electrodes 20. In other words, covering 30 may substantially surround central member 26, extension members 24 and/or electrodes 20 and, therefore, be "supported" and/or conform to the shape of the scaffold defined by central member 26, extension members 24 and/or electrodes 20 As shown in FIG. 2, when the scaffold is in an expanded configuration (e.g. extension members 24 extending radially away from central member 26), covering 30 may also be expanded, thereby conforming to the shape of the scaffold defined by central member 26, extension members 24 and/or electrodes 20.

As shown in FIG. 2, covering 30 may be ovular-shaped when expanded by the scaffold. However, it is contemplated that covering 30 may assume a variety of other shapes depending on the specific geometry and design of the scaffold. For example, covering 30 may be cylindrical, spherical, disk-shaped or the like.

In some examples disclosed herein, extension members 24 may be pivotably coupled to central member 24. In other words, extension members 24 may rotate and/or pivot with respect to central member 26. In at least some embodiments contemplated herein, extension members 24 may be able to pivot both in a distal and proximal direction with respect to central member 26. Further, extension members 24 may be able to pivot from a position in which the extension members 24 are proximal facing (e.g. positioned substantially alongside central member 26), through 180 degrees to a position in which the extension members are distally facing (e.g. positioned substantially alongside central member 26). It can be appreciated that at the halfway position (e.g. at 90 degrees), the extension members 24 may be pointing away from the longitudinal axis of central member 26. In other words, extension members may be substantially perpendicular to the longitudinal axis of central member 26.

Although FIG. 2 shows extension members 26 pointing radially away from the longitudinal axis of central member 26, it is contemplated the extension members 26 may point, align, face, etc. other directions (e.g. at other angles) with respect to the longitudinal axis of central member 26.

Figure 3:
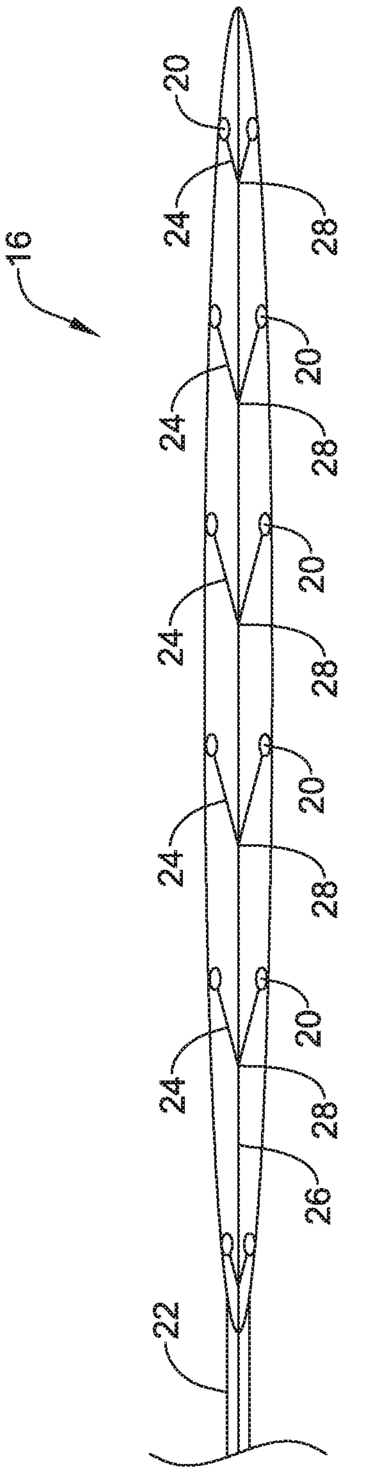
FIG. 3 is a side view of an example medical device in a collapsed configuration.

FIG. 3 shows conductive assembly 16 in a collapsed configuration. As shown in FIG. 3, extension members 24 are pivoted in a distal facing direction. In some instances, extension members 24 are folded such that they are positioned substantially alongside central member 26. In other words, extension members 24 are pivoted such that they are aligned longitudinally with central member 26. While FIG. 3 shows extension members 24 pivoted in a distal facing direction, it is contemplated that extension members 24 may, in some embodiments, be pivoted and/or aligned in a proximal facing direction.

Additionally, FIG. 3 shows covering 30 collapsed and/or folded in a corresponding configuration with distal facing/folded extension members 24. It may be desirable for covering 30 to tightly fold and/or collapse around central member 26, extension members 24 and/or electrodes 20. Covering 30 may protect the conductive assembly 16 while being delivered to a target site. For example, covering 30 may be tightly collapse around conductive assembly 16, thereby preventing extension members 24 from being caught on body lumen surfaces and/or obstructions while being delivered to a target location. Furthermore, a tightly collapsed covering 30 may allow the conductive assembly 16 to better navigate narrowed and/or constricted passages within the body (e.g. the biliary tract).

Figure 4:
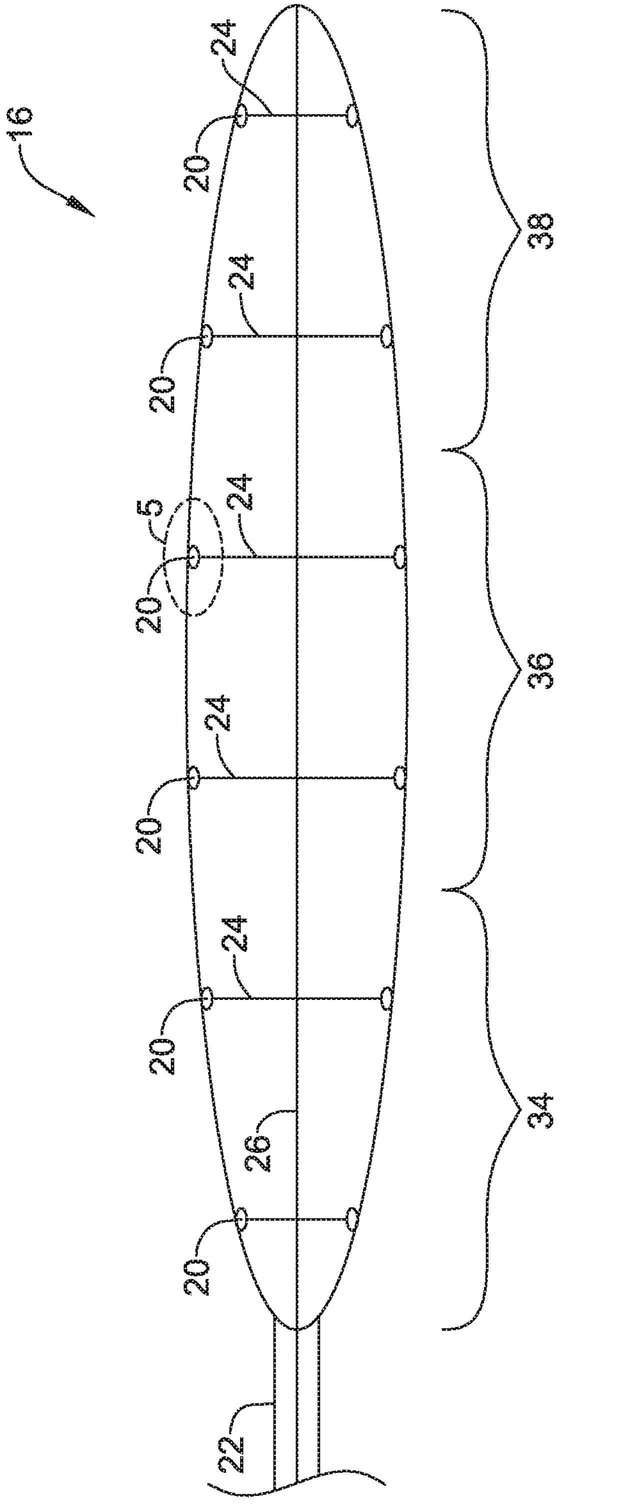
FIG. 4 is a side view of an example medical device in an expanded configuration.

FIG. 4 shows conductive assembly 16 in an expanded configuration. As shown in FIG. 4, extension members 24 may extend substantially perpendicular to the longitudinal axis of central member 26. In this configuration, extension members 24 may be fully extended from central member 26. In other words, FIG. 4 shows an example in which electrodes 20 may be farthest away (radially) from central member 26.

It is contemplated that in at least some embodiments, conductive assembly 16 may be shifted from a first collapsed position (as shown in FIG. 3) to an expanded position (as shown in FIG. 4). As discussed above, conductive assembly 16 may be positioned in a collapsed configuration for delivery to a target site, after which, it may be expanded to deliver ablative energy to a target stricture and/or lesion.

Additionally, in some embodiments disclosed herein, one or more extension members 24 may be unequal in length to one or more other extension members 24. For example, discrete attachment locations 28 may be located at proximal, middle and distal "regions" along the longitudinal axis of central member 26. FIG. 4 shows example proximal, middle and distal regions 34/36/38. As shown, the length of at least one of extension members 24 located in the proximal region 34 and distal region 38 are shorter than the length of at least one of extension members 24 located in middle region 36. Although FIG. 4 depicts the extension members 24 in the proximal and distal regions 34/38 as being substantially equal in length, it is contemplated that any of the extension members 24 positioned along central member 26 may longer or shorter than any other member along central member 26. For example, the design and arrangement of the extension members 24 may include a variety of lengths, geometries, spacing or the like. While the embodiment depicted in FIG. 4 generally shows the conductive assembly generally ovular (e.g. football) shaped, it is only an example. Other shapes, variations, designs and geometries are contemplated.

Figure 5:
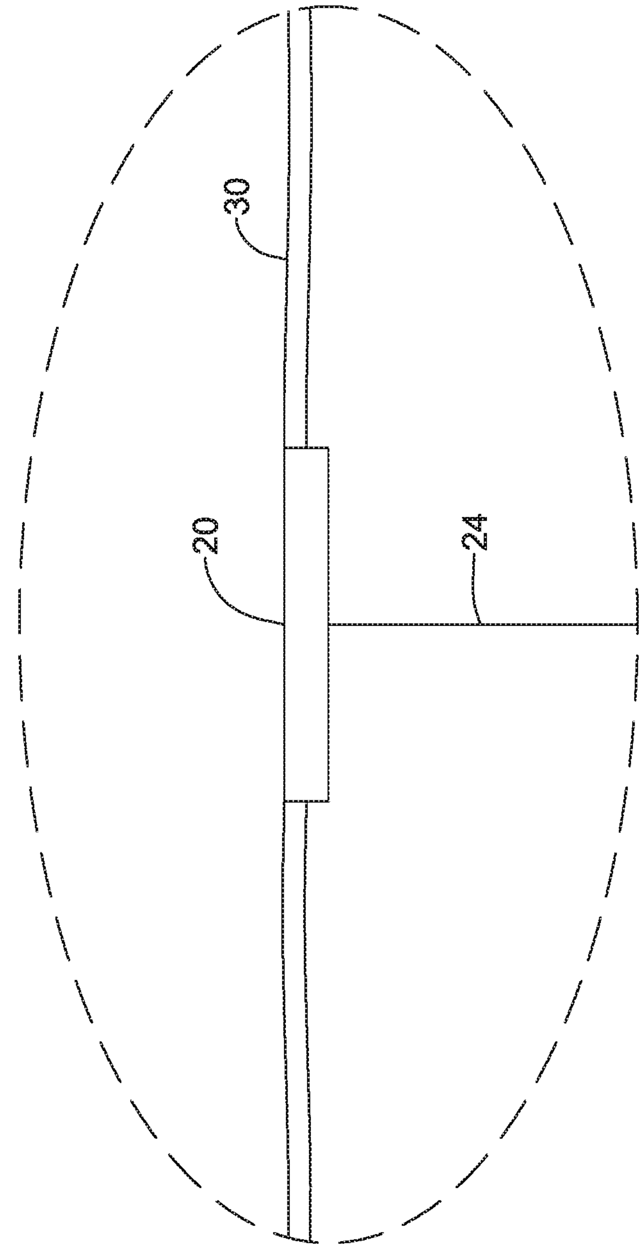
FIG. 5 is a detailed view of an example electrode of an example medical device.

FIG. 5 shows example electrode 20 located at the distal end of the extension member 24. Additionally, FIG. 5 shows electrode 20 extending at least partially through covering 30. In other words, it is contemplated in at least some embodiments disclosed herein that electrodes 20 are coupled with covering 30 such that a portion of electrode 20 extends through the wall of covering 30 and, further, that a portion of electrode 20 is substantially "flush" with the outer surface of covering 30. In some instances, electrode 20 may incorporated and/or integrated within the wall of covering 30. Although FIG. 5 shows a single electrode, it is contemplated that the above discussion applies to one or more of electrodes on conductive assembly 16.

Furthermore, although FIG. 5 depicts electrodes 20 as being substantially disk shaped, it is contemplated that electrodes 20 may be include a variety of other shapes, all or a portion of which may extend through all or a portion of covering 30. Additionally, it is contemplated that more than one electrode 20 may be located on extension members 24.

As stated above, electrodes 20 may be configured to delivery RF ablation to a stricture and/or other target site within a body lumen. For example, a conductive assembly 16 in a collapsed configuration may be advanced to within the vasculature to a target location (e.g. advanced through the biliary tree to a stricture and/lesion within the bile duct or similar structure). A clinician may then shift the conductive assembly 16 from a collapsed configuration to an expanded configuration. The expanded configuration may extend and position electrodes 20 along the surface of the stricture. Once positioned appropriately, the clinician may deliver energy (e.g. RF energy) through an electrical pathway (e.g. central member 26 and/or extension members 24) to electrodes 20. In some instances the clinician may utilize power element 18 to deliver a desired amount of energy. Furthermore, it is contemplated that one of more of electrodes 20 may be configured to operate as a bipolar electrode, unipolar electrode or both. Additionally, any combination of electrodes 20 may be multiplexed as desired.

Figure 6:
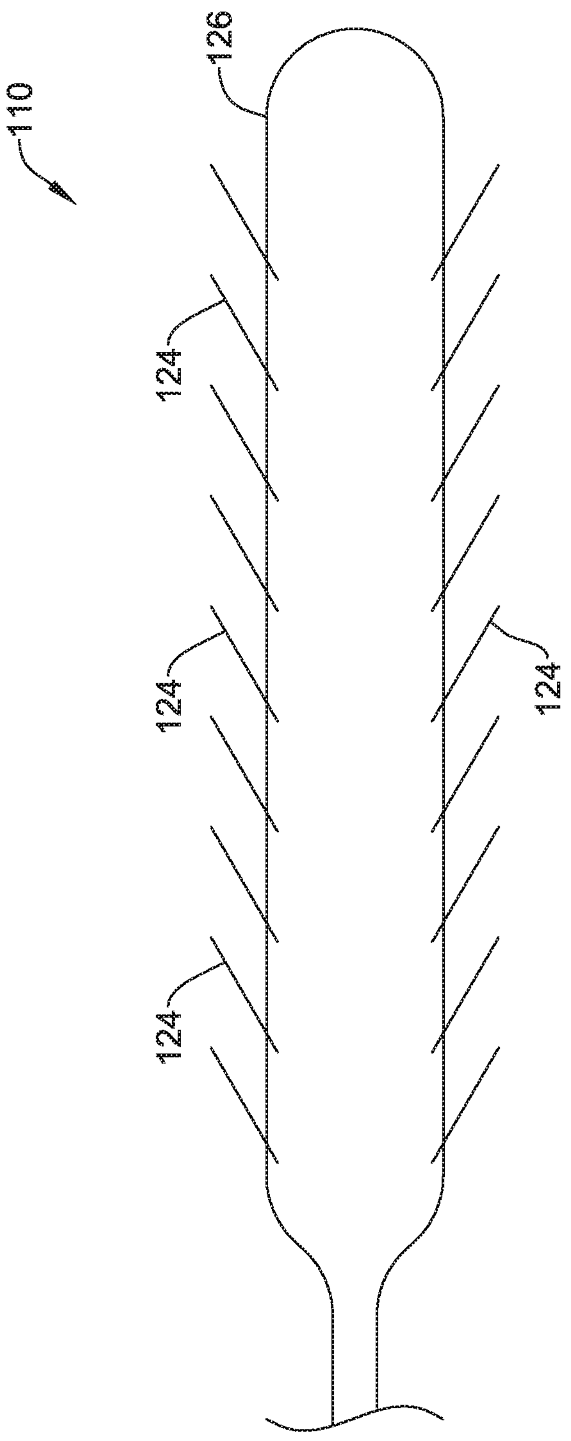
FIG. 6 is a side view of another example medical device.

FIG. 6 shows another example stricture ablation assembly 110. As shown in FIG. 6, stricture ablation assembly 110 may include a central wire 126 and multiple deployable spikes 124 extending therefrom. Deployable spikes 124 may be capable of delivering RF energy at multiple sites along the length of central wire 126. In some instances, deployable spikes may be deployed through actuation of a mechanism (e.g. handle) located proximally of stricture ablation assembly 110.

Figure 7A:
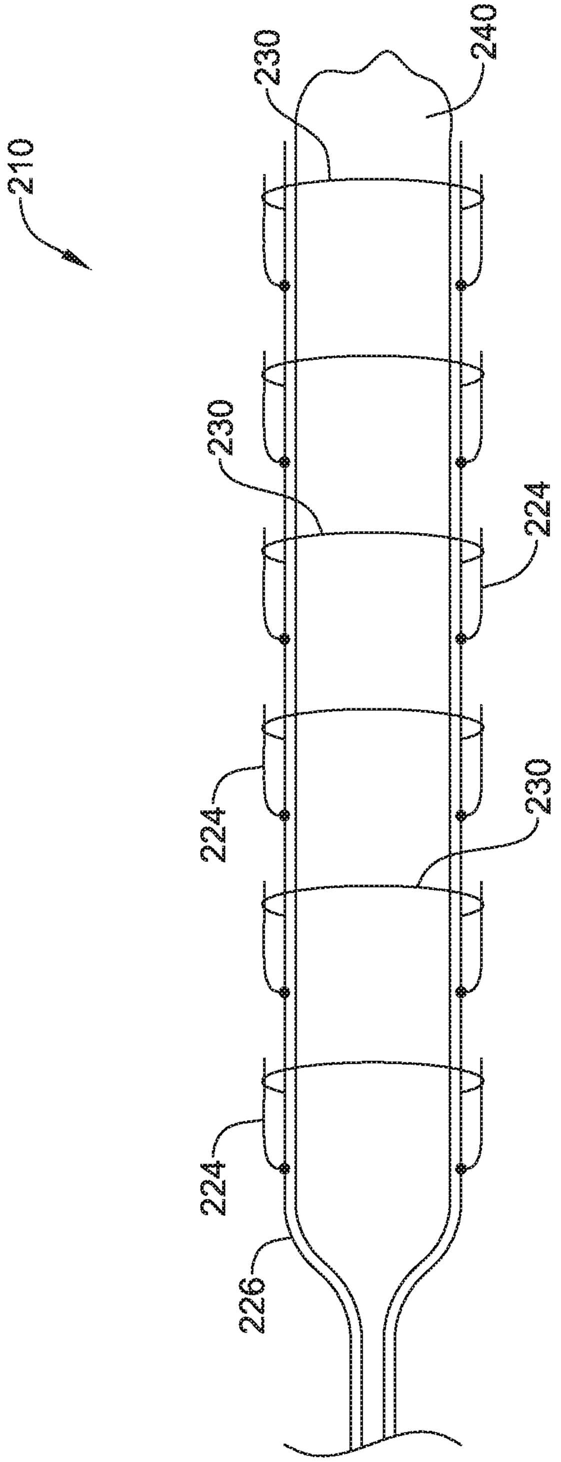
FIG. 7*a* is a side view of an example medical device in a collapsed configuration.
Figure 7B:
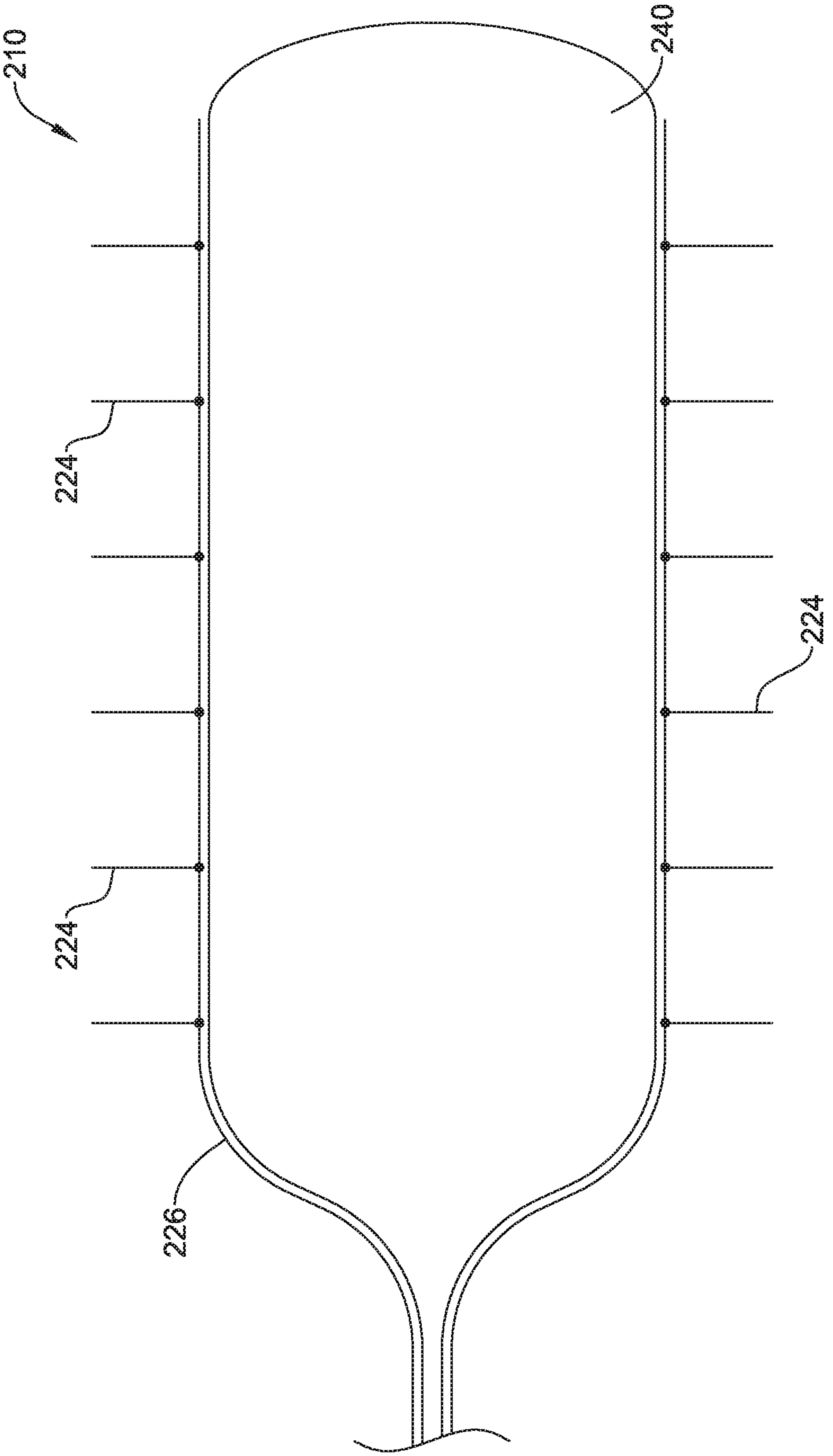
FIG. 7*b* is a side view of an example medical device in an expanded configuration.

FIGS. 7A and 7B show another example stricture ablation assembly 210. As shown in FIG. 7A, stricture ablation assembly 210 may include a central wire 226 and multiple deployable spikes 224 extending therefrom. Deployable spikes 224 may be capable of delivering RF energy at multiple sites along the length of central wire 226. Further, central wire 226 and deployable spikes 224 may be positioned on an external surface of expandable element 240 (e.g. balloon). In some examples, FIG. 7A may show stricture ablation assembly 210 in a collapsed configuration. Similar to that discussed with respect to stricture ablation assembly 10, ablation assembly 210 may be delivered to a target site in a collapsed configuration. In some instances, deployable spikes 224 may be radially constrained by wrapping members 230. Further, wrapping members 230 may include a biodegradable material.

Deployment of the stricture ablation assembly 210 may include expanding the expandable element 240 and releasing wrapping members 230 (e.g. via biodegradation). FIG. 7B shows example stricture assembly 210 after deployment. As shown in FIG. 7B, deployable spikes 224 have been released from wrapping members 230 and extend away from central wire 226. Further, expandable element 240 has been expanded, thereby shifting deployable spikes 224 radially outward. The deployable spikes 224 may penetrate directly into surrounding tissue. In some instances, the expansion of expandable element 240 coupled with the application of RF energy may allow for additional areas of a target site to be treated (e.g. ablated).

Figure 8:
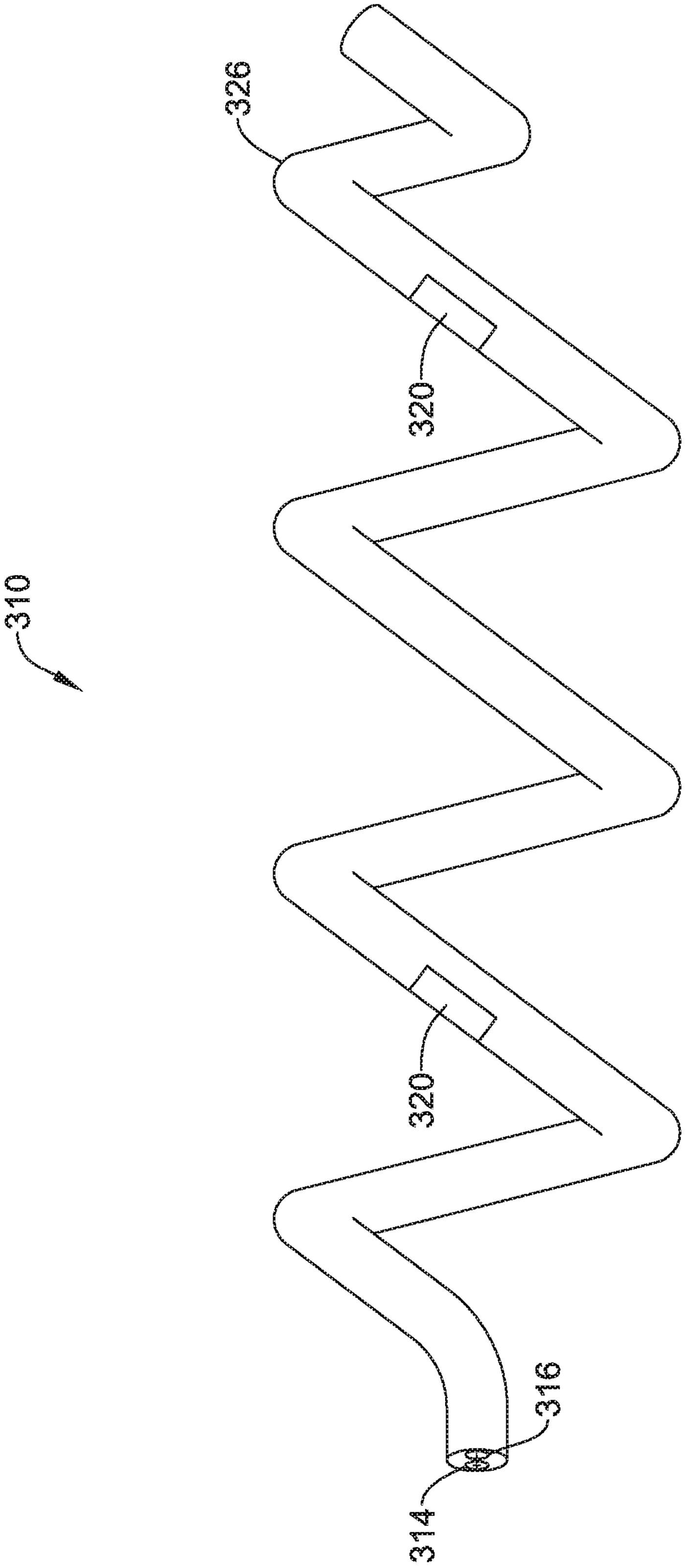
FIG. 8 is a side view of another example medical device.

FIG. 8 shows another example stricture ablation assembly 310. As shown in FIG. 8, stricture ablation assembly 310 may include a coiled wire 326. In some instances, coiled wire 326 may represent the stricture ablation assembly 310 after deployment. In some examples, coiled wire 326 may able capable of being configured in a substantially straight configuration. A straight configuration may be desirable for delivery to the target lesion. Once placed at target location (e.g. stricture), the coiled wire 326 may shift to the coiled shaped depicted in FIG. 8. In some instances, coiled wire 326 may apply RF energy directly to surrounding tissue. The coiled shaped of wire 326 may provide radial force outward against surrounding tissue.

In some instances, stricture ablation assembly 310 may include one or more conductive members 314/316 extending within coiled wire 326. Additionally, one or more of conductive members 314/316 may be configured, designed and/or operated as bipolar or unipolar conductive members. For example, in some instances conductive members 314/316 may include one bipolar conductive member and/or one unipolar conductive member positioned adjacent one another within coiled wire 326.

A portion of coiled wire 326 may be removed to expose one or more portions of conductive members 314/316. For example, FIG. 8 shows two conductive portions 320 located along a portion of coiled wire 326. Conductive portions 320 may be a portion of either bipolar conductive member or unipolar conductive member 314/316. Further, conductive portions 320 may be constructed by removing a portion of the surface of coiled wire 326 to expose conductive member 314/316. Although FIG. 8 shows two conductive portions 320, it is contemplated that any number of conductive portions may be exposed along coiled wire 326. For example, 1, 2, 3, 4, 5, 6, 7, 8, 9, 10, 20, 50, 100 or more conductive portions may be exposed. Further, conductive portions may be designed to deliver energy (e.g. RF) to adjacent tissue in either a unipolar and/or bipolar configuration.

Figure 9:
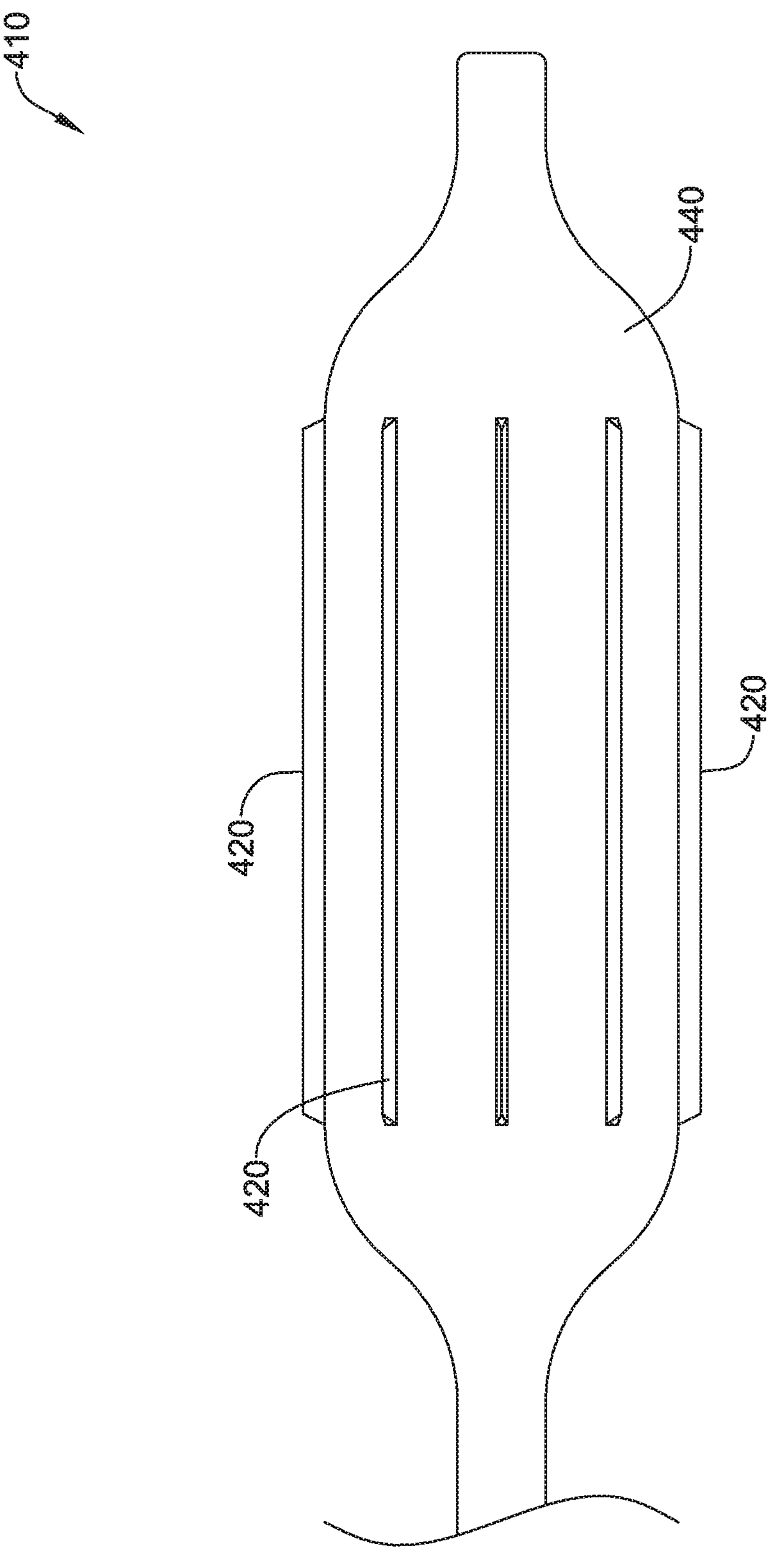
FIG. 9 is a side view of another example medical device.

FIG. 9 shows another example stricture ablation assembly 410. As shown in FIG. 8, stricture ablation assembly 410 may include elongated members 420 coupled to an expandable member 440. In some examples, elongated members 420 may include blades capable of delivering RF energy to a target site. In addition, elongated members 420 may include a shape memory material. In some instances, elongated members 420 may be aligned in a longitudinal, radial, spiral or similar configuration. In some examples, rotation of elongated members 420 may allow stricture ablation assembly 410 to “drill” through a target stricture. Stricture assembly 410 may be delivered in a compact configuration. Deployment of ablation assembly 410 may include expanding the expandable member 440 and delivering RF energy via elongated members 420.

Stricture ablation assemblies disclosed herein and/or other components of the stricture ablation assemblies may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated “linear elastic” or “non-super-elastic” which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial “superelastic plateau” or “flag region” in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed “substantially” linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of stricture ablation assemblies disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stricture ablation assemblies 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of stricture ablation assemblies disclosed herein to achieve the same result.

In some embodiments, a degree of Magnetic Resonance Imaging (MM) compatibility is imparted into stricture ablation assemblies disclosed herein. For example, stricture ablation assemblies disclosed herein, or portions thereof, may be made of a material that does not substantially distort the image and create substantial artifacts (e.g., gaps in the image). Certain ferromagnetic materials, for example, may not be suitable because they may create artifacts in an MRI image. Stricture ablation assemblies disclosed herein, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, stricture ablation assemblies disclosed herein may be made from a polymer. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:

a scaffold including a central member and a plurality of extension members extending away from the central member;

wherein the scaffold is configured to shift between a delivery configuration and an expanded configuration;

wherein the plurality of extension members includes a first extension member;

a resilient covering fully enclosing the scaffold between a proximal terminus of the resilient covering and a distal terminus of the resilient covering, the resilient covering tightly conforming to the scaffold when the scaffold is in both the delivery configuration and the expanded configuration, the resilient covering having an ovular shape in both the expanded and delivery configurations such that an exterior surface of the resilient covering continuously curves from the proximal terminus to the distal terminus; and an electrode located only at a distal end of the first extension member, wherein no other electrodes are located along the first extension member between its proximal and distal ends.

2. The medical device of claim 1, wherein the electrode extends through at least a portion of the resilient covering.

3. The medical device of claim 1, wherein the electrode is flush with an outer surface of the resilient covering.

4. The medical device of claim 1, wherein the central member has a longitudinal axis, and wherein the plurality of extension members are spaced apart along the longitudinal axis.

5. The medical device of claim 1, wherein when the scaffold is in the delivery configuration, the distal end of the first extension member is positioned substantially alongside the central member.

6. The medical device of claim 1, wherein the first extension member is configured to be shifted between distally-extending configuration and a radially-extending configuration.

7. The medical device of claim 1, wherein the first extension member is metallic.

8. The medical device of claim 1, wherein the central member includes a wire.

9. The medical device of claim 1, wherein the resilient covering includes a polymer.

10. The medical device of claim 1, wherein the first extension member has a first length, wherein the plurality of extension members includes a second extension member having a second length, and wherein the first length is different than the second length.

11. The medical device of claim 1, wherein the central member includes a proximal portion, a distal portion and a middle portion located between the proximal and distal portions, wherein each of the proximal, middle and distal portions include at least one extension member attached thereto, and wherein the lengths of the at least one extension member attached to the proximal and distal portions are shorter than the at least one extension member attached to the middle portion.

12. The medical device of claim 1, wherein the electrode includes a bipolar electrode, a unipolar electrode, or both.

13. The medical device of claim 1, wherein the electrode is coupled to an energy source.

14. A medical device, comprising:

a conductive assembly including a central member and a plurality of extension members coupled to the central member;

a resilient covering fully enclosing the conductive assembly, the covering having an ovular shape with an exterior surface curving proximally toward a proximal terminus of the covering from a radial outermost extent of the covering and curving distally from the radial outermost extent of the covering toward a distal terminus of the covering;

wherein the plurality of extension members includes a first extension member and a second extension member;

wherein the first extension member has a first end and a free end, the free end being free from attachment to the central member;

an electrode coupled only to the free end of the first extension member, wherein no other electrodes are located along the first extension member between its first end and free end;

wherein the first extension member has a first length;

wherein the second extension member has a second length that is shorter than the first length; and wherein the second extension member is disposed distally of the first extension member.

15. The medical device of claim 14, wherein the plurality of extension members are pivotably coupled to the central member.

16. The medical device of claim 14, wherein the central member includes a plurality of discrete attachment locations corresponding to each of the plurality of extension members and wherein each of the plurality of extension members is coupled to the central member at a corresponding discrete attachment location.

17. The medical device of claim 14, wherein the plurality of extension members includes a metal.

18. The medical device of claim 14, wherein the covering includes a polymer.

19. The medical device of claim 14, wherein the first extension member is configured to be shifted between distally-extending configuration and a radially-extending configuration.

20. A medical device, comprising:

a scaffold including a central member and a plurality of extension members pivotably coupled to the central member;

wherein the plurality of extension members includes a first extension member having a first length and a second extension member disposed distally of the first extension member and having a second length that is shorter than the first length;

a covering surrounding and fully enclosing the scaffold between a proximal terminus of the covering and a distal terminus of the covering, the covering having an ovular shape such that an exterior surface of the resilient covering continuously curves from the proximal terminus to the distal terminus; and an electrode located at a free end of each of the first and second extension members, wherein no other electrodes are located along the length of the first and second extension members, wherein each electrode extends through at least a portion of the covering to a position that is flush with an outer surface of the covering.

* * * * *